(12) United States Patent
Morseman et al.

(10) Patent No.: US 7,256,050 B2
(45) Date of Patent: Aug. 14, 2007

(54) HIGH FLUORESCENT INTENSITY CROSS-LINKED ALLOPHYCOCYANIN

(75) Inventors: John Peter Morseman, Columbia, MD (US); Mark Wesley Moss, Baltimore, MD (US); F. C. Thomas Allnutt, Port Deposit, MD (US)

(73) Assignee: Martek Biosciences Corp., Columbia, MD (US)

( * ) Notice: Subject to any disclaimer, the term of this patent is extended or adjusted under 35 U.S.C. 154(b) by 0 days.

(21) Appl. No.: 09/882,376

(22) Filed: Jun. 18, 2001

(65) Prior Publication Data

US 2002/0061601 A1 May 23, 2002

Related U.S. Application Data

(60) Provisional application No. 60/211,978, filed on Jun. 16, 2000.

(51) Int. Cl.
*G01N 21/76* (2006.01)

(52) U.S. Cl. ............... 436/172; 436/164; 436/546; 435/7.92

(58) Field of Classification Search ........ 436/501, 436/518, 546, 800, 537, 164, 166, 172; 435/7.1, 435/7.92, 7.93–7.94
See application file for complete search history.

(56) References Cited

U.S. PATENT DOCUMENTS

| | | | |
|---|---|---|---|
| 4,857,467 A | 8/1989 | Sreekrishna et al. | 435/255 |
| 5,627,074 A | 5/1997 | Mathis et al. | 436/518 |
| 5,714,386 A | 2/1998 | Roederer | 436/546 |
| 6,232,130 B1 * | 5/2001 | Wolf | 436/501 |

FOREIGN PATENT DOCUMENTS

| | | |
|---|---|---|
| EP | 235112 | 9/1987 |
| WO | WO 93 05163 | 3/1993 |
| WO | WO 94 20627 | 9/1994 |
| WO | WO 96 31612 | 10/1996 |
| WO | WO 97 39106 | 10/1997 |

OTHER PUBLICATIONS

Park et al., (Homogeneous Proximity Tyrosine Kinase Assays: Scintillation Proximity Assay versus Homogeneous Time-Resolved Fluorescence, Analytical Biochemistry 269, 94-104 (1999)).*
Ong et al., (Crosslinking of allophycocyanin, Physiol. Veg., 1985, 23 (1) 777-787).*
Huang et al., (Kinetics of Allophycocyanin's Trimer-Monomer Equilibrium, Biochemistry), 1987, 26, 243-245.*
MacColl (Stability of Allophycocyanin's Quat rnary Structure, Archives of Biochemistry and biophysics, vol. 223, No. 1, May 1993, pp. 24-32).*
MacColl et al., (Phycobiliproteins, CRC Press, 1987).*
Kolb et al., Use of Novel Homogeneous Fluorescent Technology in High Throughput Screening, Journal of Biomolecular Screening, vol. 1, No. 4, 1996 p. 203-210.*
Mellor et al., Development of a CD28/CD86 (B7-2) Binding Assay for High Throughput Screening by Homogeneous Time-Resolved Fluorescence, Journal of Biomolecular Screening, vol. 3, No. 2 1998, pp. 91-99.*
Zaslavskaia, et al; "Trophic conversion of an obligate photoautotrophic organism through metabolic engineering", Science, vol. 292, 2073-2075, (2001).
Vazhappilly, et al., "Eicosapentaenoic acid and docosahexaenoic acid production potential of microalgae and their heterotrophic growth", Journal of the American Oil Chemists Society, vol. 75, 393-397 (1998).
Hu, Dongli et al., "The *C. reinhardtii* CF$_1$ with the mutation βt168S has high ATPase activity", FEBS Letters, vol. 421, 65-68 (1998).
Hallmann, et al., The *chlorella* hexose/H$^+$ symporter is a useful selectable marker and biochemical reagent when expressed in *Volvox*, Proc. Natl. Acad. Sci USA, vol. 93, 669-673, (1996).
Chen, Feng "High cell density culture of microalgae in heterotrophic growth", TIBTECH, vol. 14, 421-426, (1996).
Zaslavskaia, Lioudmila A.et al., "Transformation of the diatom *Phaeodactylum tricornutum* (bacillariophyceae) with a variety of selectable marker and reporter genes", J. Phycol., 36, 379-386, (2000).
Lewin, J. et al., "Utilization of glutamate and glucose for heterotrophic growth by the marine Pennate diatom *Nitzschia laevis*", Marine Biology, 47, 1-7, (1978).
Droop M.R., "Heterotrophy of carbon", Stewart, ed., Botanical Monographs, vol. 10, Chapter 19, 530-559, (1975).
Johan Hellebust, et al.., "Heterotrophic Nutrition", Werner, ed., Botanical Monographs, vol. 13, Chapter 6, 169-197 (1997).
Brejc, K., et al., "Isolation, Crystallization, Crystal Structure Analysis and Refinement of Allophycocyanin from the Cyanobacterium *Spirulina platensis* at 1.3 Å Resolution," J. Mol. Biol. 249(2):424-440 (1995).
Hanke, J., et al., Discovery of a Novel, Potent and Src Family-Selective Tyrosine Kinase Inhibitor, J. Biol. Chem. 271(2):695-701 (1996).
Hemmilä, I., et al., "Europium as a Label in Time-Resolved Immunofluorometric Assays," Anal. Biochem. 137(2):335-343 (1984).

(Continued)

*Primary Examiner*—Long V. Le
*Assistant Examiner*—Gary W. Counts
(74) *Attorney, Agent, or Firm*—Hunton & Williams LLP (57) ABSTRACT

In a method for quantitating an analyte by measuring time resolved transfer of fluorescence energy to or from a label quantitatively associated with the analyte, the present invention provides an improvement comprising measuring the energy transferred from donor compounds having the ability to absorb light energy and then transfer this energy to cross-linked allophycocyanin in a time-resolved manner, where the cross-linked allophycocyanin used according to this invention has not been exposed to strongly chaotropic agents after cross-linking.

12 Claims, 6 Drawing Sheets

OTHER PUBLICATIONS

Massillon, D., et al., "Identification of the Glycogenic Compound 5-Iodotubercidin as a General Protein Kinase Inhibitor," Biochem. J. 299:123-128 (1994).

Mathis, G., "Rare Earth Cryptates and Homogeneous Fluorimmunoassays with Human Sera," Clin. Chem. 39(9):1953-1959 (1993).

Moore, K. et al., "Single Molecule Detection Technologies in Miniaturized High Throughput Screening: Fluorescence Correlation Spectroscopy," J. Biomol. Screening 4(6):335-353 (1999).

Morris, C. et al., "Fluorescence Resonance Energy Transfer (FRET) as a Direct Method for the Epitope-Specific Characterisation of Anit-Platelet Antibodies," British Journal of Haematology 101(Supp. 1):88 (1998) (Abstract 264).

Roederer, M., et al., "Cy7PE and Cy7APC: Bright New Probes for Immunofluorescence," Cytometry 24(3):191-197 (1996).

Sportsman, J., et al., "Miniaturization of Homogeneous Assays Using Fluorescence Polarization," Drug Discovery Today: HTS Supplement 1(1):27-32 (2000).

* cited by examiner

Figure 1A. Fluorescence emission spectra of 500 ng/mL APC stored for 0 h (solid line) and 2 h (dotted line) at room temperature. Note that at 0 h the emission maximum was 660 nm while after 2 h it shifted to 642 nm and lost 50% of it's fluorescence emission intensity.

Figures 1B & 1C. Fluorescence emission spectra for SL-APC (B: left graph) and XL-APC (C: right graph) stored at 500 ng/mL in PBS for 0 h (solid line) and 2 h (dotted line).

Figure 2: Effect of high temperature (65°C) on APC, SL-APC and XL-APC stability. Change in relative fluorescence intensity (CPS) at 660 nm between Native APC (dot/dashed line), SL-APC (solid line) and XL-APC (dashed line) over time when stored at 65°C.

Figure 3

Figure 4. Detection of Phosphorylated Poly-GAT with Europium labeled Anti-Phosphotyrosine IgG (PY20) and SL-APC labeled streptavidin or a commercially availabe XL-APC labeled streptavidin. Poly-GAT was phosphorylated with a src-tyrosine kinase and then titrated from 0 ng to 12 ng. Positive phosphorylation was measured as a ratio using two wavelengths (620 & 650 nm) as previously described (Mathis, *Clin. Chem.*, 41:1391-1397, 1995).

HIGH FLUORESCENT INTENSITY CROSS-LINKED ALLOPHYCOCYANIN

CROSS REFERENCE TO RELATED APPLICATIONS

The present application claims priority from U.S. Provisional Patent Application No. 60/211,978 filed Jun. 16, 2000, entitled "High Fluorescent Intensity Cross-Linked Allophycocyanin." The disclosure of this application is incorporated, by reference, in its entirety.

BACKGROUND

1. Field of the Invention

This invention relates to cross-linked allophycocyanin, its production and its use in fluorescent assays of various formats.

2. Related Art

Allophycocyanin (APC) is a fluorescent light harvesting protein unique to cyanobacteria and red algae and a member of the phycobiliprotein family of direct fluorescent dyes. APC is excited in the low 600 nm's (650 nm maximum) and emits with a maximum intensity at 660 nm. APC has become more common as a fluorescent label in flow cytometry because of the emergence of multi-laser instrumentation for multi-color detection (e.g., with Helium/Neon laser excitation) and production of tandem dyes for multiplexed assays (Roederer, et al., (1996), *Cytometry* 24, 191–197). In addition, APC is used as an acceptor from lanthanide dyes for high throughput time resolved fluorescent assays being increasingly used for drug discovery (Park, et al. (1999), *Analytical Biochemistry* 269, 94–104; Moore, et al. (1999), *J Biomol Screening* 4, 205–2143; Morris, et al. (1998), *British Journal of Haematology* 101, 88).

Unfortunately, native APC dissociates into monomers under most assay conditions (e.g., low protein and buffer concentrations). Native APC (herein referred to as "APC") consists of six phycobiliprotein subunits, made up of three dimers which each contain an alpha and a beta subunit. APC dissociation results in a shift in fluorescence emission from 660 nm and a drop in fluorescence intensity. Dissociation occurs at low concentrations, such as concentrations under 10 μg/mL of APC. Dissociation makes the native APC incompatible for assay conditions commonly used for flow cytometry, microplate assays and high throughput screening (HTS) applications.

Cross-linked and stabilized allophycocyanin preparations (herein referred to as XL-APC) were developed by Glazer and Ong to make this dye more suitable for use in immunoassay (Ong L J & Glazer A N (1985) *Physiol Vég* 23(1), 777–787). Those authors took a standard preparation of APC and treated it with a chemical cross-linking agent, 1-ethyl-3-(3-dimethylaminopropyl) carbodiimide (EDAC), such that an average of one alpha subunit was linked to one beta subunit in a covalent manner in each APC trimer (which contains three of each subunit type). The product was then denatured under 8 M urea to dissociate it into its component parts: alpha and beta monomeric subunits and covalently linked alpha-beta dimeric subunits. The covalently-linked dimers were separated from the monomers using denaturing gel filtration, and then the dimers were placed in an environment that allowed them to reassociate into an $(\alpha\beta)_3$ complex that displayed unusually high stability compared to native APC. The resultant material is referred to herein as XL-APC. This material has increased stability in the presence of chaotropic salts (such as sodium perchlorate) or at low concentrations of buffer compared to native APC. When run on a denaturing gel, most of the material runs as a single band that is the covalently linked $\alpha\beta$ dimer. In the current art, the higher the percentage of cross-linked $\alpha\beta$ dimeric subunits, the better the utility of the XL-APC. A number of XL-APC preparations are commercially available that have various percentages of covalently stabilized $\alpha\beta$ dimer in the final product, all greater than 50%.

Figure 1A:
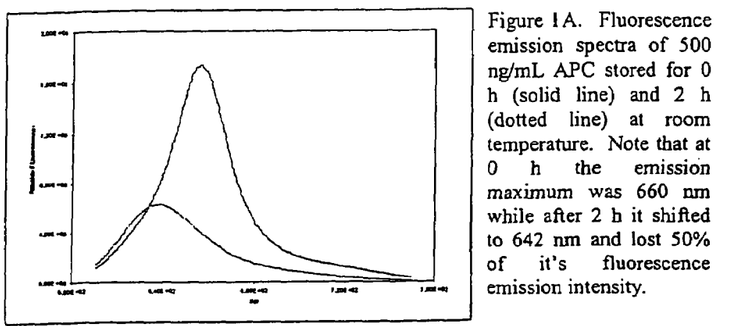
FIG. 1 shows fluorescence emission spectra for native APC (A), SL-APC (B) and XL-APC (C) and its change over time stored at low phosphate concentration.
Figure 1B:
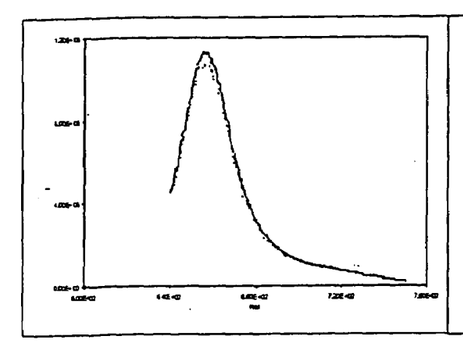
Figure 1C:
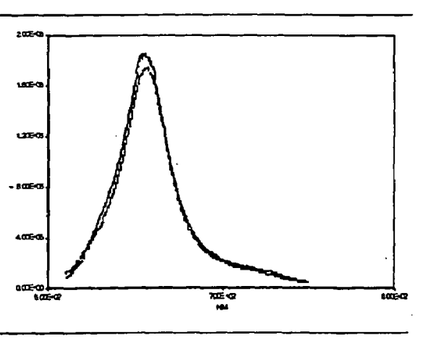

As seen in FIGS. 1A & 1C, XL-APC has a reduced ration of fluorescence at 650/620 nm versus the native APC. This also is reflected in a reduced ratio of the 650 nm absorbance of APC to the 280 nm absorbance peak reflecting total protein, an indication that the absorbance per molecule has been decreased. One commercially available preparation of XL-APC is called XL665™ (CIS Bio), and this material demonstrates the same decreased ratios of 650/620 fluorescence and 650/280 absorbance observed in the other XL-APC preparations now commercially available.

SUMMARY OF THE INVENTION

The present invention provides an improved method for quantitating an analyte by measuring fluorescence emission from a fluorescent label specifically associated with the analyte. The improvement comprises binding the analyte directly or indirectly to a cross-linked allophycocyanin molecule, where the cross-linked allophycocyanin has not been exposed to strongly chaotropic materials after cross-linking and preferably where uncross-linked monomeric subunits have not been removed from the chemically stabilized allophycocyanin preparation.

In particular embodiments, the invention provides an improved method for quantitating an analyte by measuring time resolved fluorescence of a label quantitatively associated with the analyte. Specifically, this method comprises measuring energy absorbed by donor compounds having the ability to absorb light energy and then transferred to cross-linked allophycocyanin by detecting allophycocyanin fluorescence in a time-resolved manner, and the improvement lies in using cross-linked allophycocyanin which has not been exposed to strongly chaotropic agents after cross-linking. In prefered embodiments, the donor molecule comprises a metal, more preferably a lanthanide series metal. Suitable metals include europium or ruthenium, which may be chelated or in a cryptate.

This invention also provides a method for performing a specific binding assay comprising (1) contacting a sample comprising an analyte with a specific binding partner; and (2) determining the amount of the analyte present in the sample by means of its ability to specifically bind to the specific binding partner, where a component of the assay is detectably labeled with a signal-generating system comprising intramolecularly cross-linked allophycocyanin. The detectably labeled assay component may be selected from the group consisting of: the specific binding partner and reagent molecules having the same binding specificity as the analyte. One of the intramolecularly cross-linked allophycocyanin preparations of this invention (herein referred to as SL-APC) has at least 20% but less than 50% of all alpha subunits of the allophycocyanin molecules linked to no more than one beta subunit, and preferably, the SL-APC cross-linked allophycocyanin has not been exposed to strongly chaotropic agents after cross-linking. Another of the intramolecularly cross-linked allophycocyanin preparations of this invention (herein referred to as GL-APC) signal generating systems of this invention has at least 50% but less than 75% of all alpha subunits of the allophycocyanin molecules linked to no more than one beta subunit, and preferably, the GL-APC cross-linked allophycocyanin has not been exposed to strongly chaotropic agents after cross-linking. Further, the absorbance spectrum of the cross-linked allophycocyanin preparations is characterized by a ratio of areas under the absorbance spectrum between 500–700 nm to the area between 250–300 nm of at least 4. The inventors have found that the intramolecularly cross-linked SL-APC exhibits enhanced time-resolved fluorescent energy transfer from europium compared to commercially available XL-APC conjugates.

In a method for quantitating an analyte by measuring time resolved transfer of fluorescence energy to or from a label quantitatively associated with the analyte, the present invention provides an improvement comprising measuring the energy transferred from donor compounds having the ability to absorb light energy and then transfer this energy to cross-linked allophycocyanin in a time-resolved manner, where the cross-linked allophycocyanin used according to this invention has not been exposed to strongly chaotropic agents after cross-linking. The donor compounds may have at least two distinct donor species and the distinct donor species may have different fluorescence lifetimes. The distinct donor species may absorb at the same wavelength. In another embodiment the distinct donor species may have different absorption spectrum. In another embodiment, the distinct donor species forming donor/acceptor pair may have the same lifetime and color but being distinguishable by fluorescent intensity.

DETAILED DESCRIPTION OF THE EMBODIMENTS

Chemical modification increases APC thermal stability and stability in low buffer and protein concentrations, while maintaining the fluorescent and spectral properties as well as the molecular weight of the native dye. The improved physical stability of chemically and intra-molecularly cross-linked APC according to this invention makes it compatible with most common assay formats.

This invention produces two formats of chemically stabilized APC, designated SL-APC (first format) and GL-APC (second format) herein. The first format is functionally the same as the second format cross-linked APC in its spectral characteristics, thermal stability, fluorescence intensity and other functional qualities. On a denaturing PAGE gel, the first format SL-APC runs as at least 20%, typically up to 50%, cross-linked, while the second format GL-APC runs at least 50%, typically greater than 75%, cross-linked. Thus, the first format offers the same assay performance as the second format at a lower production cost per use.

The two invention formats of cross-linked APC (SL-APC & GL-APC) were compared to commercially available cross-linked allophycocyain (XL-APC) under a variety of conditions. All three dyes provided similar results. Cross-linked APC (SL-APC & GL-APC) according to this invention has equivalent and improved temperature tolerance and ability to withstand chaotropic salts versus native APC. These improved physical characteristics make SL-APC and GL-APC products more suitable for use in specific binding assays than native APC. The SL-APC and GL-APC of this invention, along with a prior art XL-APC, were run on a time resolved fluorescence assay for tyrosine kinase, and both GL-APC and SL-APC provided significantly improved results over XL-APC. SL-APC and GL-APC according to this invention resists 10% DMSO with little or no change over extended exposure to this reagent.

One part of the invention is a simpler method to produce a chemically stabilized APC product that provides better sensitivity in assays while maintaining the same functional (e.g., stability) properties. This SL-APC preparation is made by treating the native APC with 1-ethyl-3-[3-dimethylaminoproply]carbodiimide hydrochloride (EDAC) or similar cross-linking agent such that it stabilizes the αβ dimer, as previously observed. Suitable cross-linking agents include N,N'-dicyclohexylcarbodiimide (DCC; a zero length carbodimide), 4-[p-azidosalicylamido]butylamine (ASBA; a crosslinker that is photoreactive towards amine and hydroxyl groups, used with EDC), N-[ε-trifluoroacetylcaproyloxy]succinimide ester (TFCS; an amine reactive crosslinker), dimethylsuberimidate (DMS, an amine reactive crosslinker), and glutaraldehyde (GA) or formaldehyde (FA) (in low concentrations). Cross-linking conditions are designed to achieve an average of one cross-linked dimer per APC trimer, or preferably, between one and two cross-linked dimer per APC trimer, on average. In contrast to the prior art, the preparation is not treated with chaotropic agents or other procedures to remove monomeric subunits which have not been conjugated as dimers. At this point, the stability of the material is functionally the same as XL-APC in the buffer conditions used in binding assays, yet it provides better signal than previously observed with commercially available XL-APC preparations. It does not denature with 1 M sodium perchlorate but on denaturation with 8 M urea and electrophoresis it only shows about 20–50% dimer formation.

The other part of the invention is an improvement in the method to produce fully cross-linked APC, such that the 650/620 ratio and 650/280 ratio of the native APC is maintained. In this method, strong denaturants such as 8 M urea are not used to dissociate the partially cross-linked APC after EDAC treatment. Strongly denaturing chaotropic agents are defined herein as agents having more strongly denaturing effect than 1.5 M sodium perchlorate, and preferably as equivalent to 6 M or greater urea or guanidine HCl.

Instead of the strongly denaturing treatment used in preparation of XL-APC (as described by Ong & Glazer 1985 *Physiol. Veg.* 23(1):777–787), a more gentle denaturant that does not affect the final 650/620 and 650/280 nm ratio is used to provide GL-APC, resulting in a fluorochrome more similar to the native dye than the commercially available XL-APC. Typical denaturants which may be used in this format are sodium perchlorate, preferably at concentrations of about 1 M.

Figure 4:
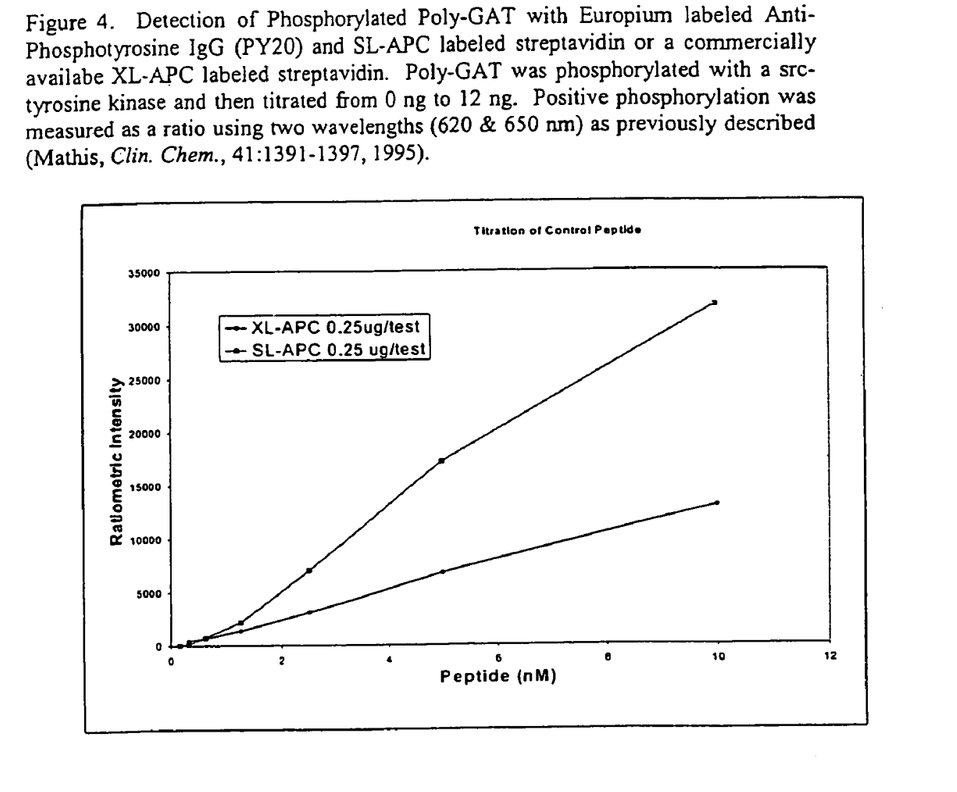
FIG. 4 shows detection of phosphorylated poly-GAT in a time-resolved fluorescence energy transfer (TR-FRET) homogeneous assay format with europium labeled anti-phosphotyrosine IgG (PY20) as the donor and SL-APC labeled streptavidin as the acceptor compared to a commercially available XL-APC streptavidin as the acceptor.

The SL-APC and GL-APC, when conjugated to streptavidin (SA), gave surprising results in homogeneous time resolved fluorescence (HTRF) experiments on the DISCOVERY microplate reader. These data (as shown in FIG. 4) compare this material to a commercially available XL-APC called XL665. In all cases, the cross-linked SL-APC:SA and GL-APC:SA conjugates of this invention proved to be better than the commercially available XL-APC:SA conjugates in detection of phosphorylated tyrosine standard peptides. In this assay, biotinylated peptides that were phosphorylated at least one tyrosine on each peptide were titrated in a homogeneous assay using either SL-APC:SA of this invention or XL-APC:SA to immobilize the peptide and $Eu^{3+}$ labeled anti-phosphotyrosine IgG to detect the phosphorylated tyrosine on the peptide. On binding of the $Eu^{3+}$ labeled antihosphotyrosine IgG, fluorescent energy transferred to the cross-linked APC from the $Eu^{3+}$ in a time resolved manner.

Cross-linked APC prepared by either format of this invention (SL-APC or GL-APC) may be further conjugated to various assay components. For use in specific binding assays, cross-linked APC can be conjugated to ligands, receptors, and/or signal-generating molecules by one-step, two-step, or multi-step methods.

Any assay format known in the art may be utilized, including without limitation, homogeneous assays, heterogeneous assays, competitive assays, and sandwich assays. In homogeneous assays, binding of the two binding partners (e.g., ligand and receptor) influences activity of the label; no separation of bound and unbound reagents is required for measurement. In heterogeneous assays, separation of bound and free reagents is required to determine the amount of binding which has occurred. Quantification of such assays can be accomplished by either photometric, fluorometric or optoelectronic means. Alternatively, qualitative results can be obtained by visual inspection.

A protein or gene product analyte can be quantitated in a biological fluid, such as serum, plasma, effusions, ascites, urine, cerebrospinal fluid, semen, breast aspirates and fluids of ovarian origin, using any protein detection method known in the art of fluorescent assay. Preferred methods employ immunological detection means. These include: immunodiffusion or immunoelectrophoretic assay and the like. Plasma should be anti-coagulated before use, as is known in the art. Cellular elements and lipid may be removed from fluids (e.g., by centrifugation). For dilute fluids, such as urine, protein may be concentrated (e.g., by ultra-filtration or salting-out).

Increasing detection sensitivity, as evidenced in an improved signal/background (s/b), signal/noise ratio (s/n) and lower limit of detection (LOD), is key in reducing overall assay cost. The major driving force in high throughput screening is to reduce the cost per test while obtaining an equal or higher density of information. Miniaturization has led the way in this attack on the cost of HTS assays (Sportsman & Leytes 2000 *Drug Discovery Today: HTS Supplement* 1(1), 27). Many approaches are possible such as chemiluminescence, chemifluorescence, calorimetric, direct fluorescent detection, fluorescence polarization, and time-resolved fluorescence energy transfer. However, the feature that makes an assay desirable versus others is its ease of use in homogeneous formats.

While the enzyme-based assays are currently being used to some extent, they suffer problems associated with requiring multiple steps, reagents and additions. Fluorescence polarization (FP) has potential (in that it is homogeneous) but is limited by low sensitivity that necessitates high-end equipment. Additionally, FP relies on small fluors that do not have general applicability. Direct fluorescence and time-resolved fluorescence offer high sensitivity and flexibility. Direct fluorescence has associated high backgrounds that the TR-FRET assays circumvent using a temporal separation between the actinic illumination and detection steps.

Although detection dye is not the major contributing factor in the cost of assays, a more sensitive dye could provide a higher signal/noise ratio enabling further assay miniaturization, significantly affecting the final cost per test. Improvement in the s/n ratio allows smaller assay volumes, hence cutting the cost in overall material consumption (both sample and reagent).

This invention provides novel fluorescent forms of APC that provide an advantage in sensitivity in homogeneous time-resolved fluroescence (HTRF) compared to commercially available forms of this dye. Thus, this invention provides additional sensitivity that could lower the limit of detection of assays using HTRF and time-resolved fluorescence (TRF). In addition, this invention provides better spectral properties than those observed with the commercially available materials. The material prepared according to this invention is a direct replacement for XL-APC now commercially available. The material of this invention can be used as the commercial material is used (e.g., in HTRF, TRF, flow cytometry, microplate immunoassays etc.). The dye of this invention is suitable for use with any known format for FRET. These formats include:

Use in homogeneous FRET.

Use in homogeneous FRET with other donor/acceptor pairs where the donor/acceptor pairs can be temporally separated. Different fluorescent lifetimes can be used to discriminate or discern between donor/acceptor pairs of the same wavelength.

Use in multiplexing, where fluorescent lifetime is temporally the same but the donor/acceptor pairs are of different and spatially separated wavelengths.

Use in multiplexing where donor/acceptor pairs are of the same lifetime and color but can be separated by intensity The making of tandem donor/acceptor dyes, which can be used for fluorescent polarization assays due to increased lifetime of SL-APC Europium conjugate.

Preferred donors include lanthanide chelates, especially cryptates (Mathis, 1993 *Clin. Chem.* 39: 1953–1959), and terpyridine chelates (Hemmila et al., 1984, *Anal. Biochem.* 137: 335–343).

SL-APC unexpectedly provided the same functional stability as the commercially available XL-APC while delivering higher sensitivity than a comparable commercially available standard (XL665 labeled streptavidin). Comments from a beta test indicated that it was very bright compared to the XL665.

FIG. 2A illustrates the fluorescence emission spectra of APC at 500 ng/ml where solid line represents APC stored for 0 h and the dotted line is APC stored at room temperature for 2 h. Note that at 0 h, the emission maximum was 660 nm while after 2 h the emission shifted to 642 nm and lost 50% of it's fluorescence emission intensity. In FIG. 2B the solid line illustrates the fluorescence emission spectra for SL-APC stored at a concentration of 500 ng/ml in PBS for 0 h and the dotted line is the emission spectra of the solution after being stored for 2 h. Similarly, in FIG. 2C the solid line illustrates the fluorescence emission spectra for XL-XPC stored at a concentration of 500 ng/ml in PBS for 0 h and the dotted line is the emission spectra of the solution after being stored for 2 h.

Figure 3:
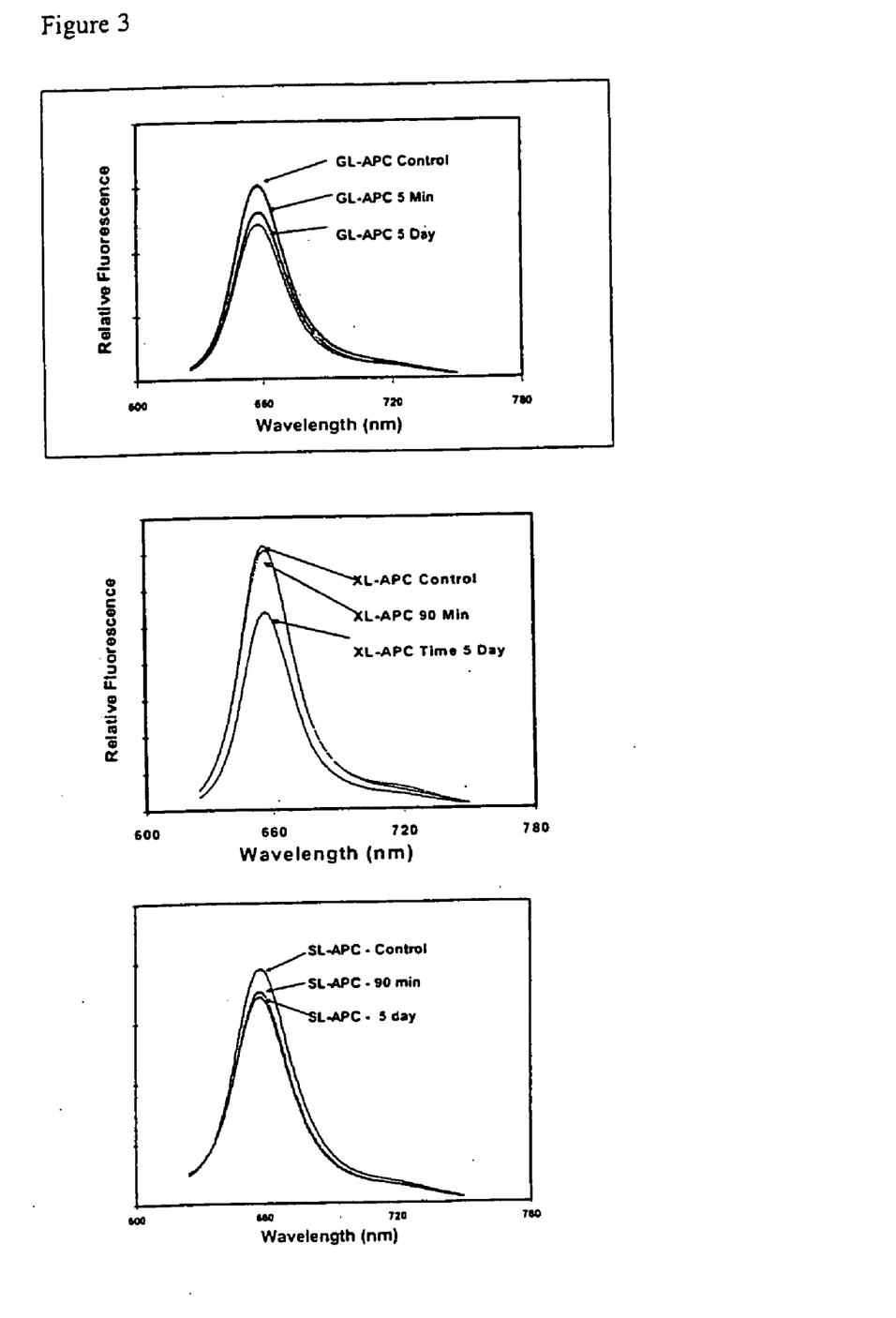
FIG. 3 shows fluorescence emission spectra for SL-APC, GL-APC and XL-APC stored in dimethyl sulfoxide for varying lengths of time.

FIG. 3 illustrates the effect of high temperature (65° C.) on APC, SL-APC, and XL-APC stability. The graphs illustrates the decrease in % of initial fluorescence or change in relative fluorescence intensity (CPS) (measured at 660 nm) over time when Native APC, SL-APC, and XL-APC when stored at 65° C.

FIG. 4 illustrates the emission spectra for GL-APC, when stored in dimethyl sulfoxide at 5 mm and 5 days as compared to a control. Additionally, FIG. 4 illustrates the emission spectra for XL-APC and SL-APC when stored in dimethyl sulfoxide at 90 mm and 5 days as compared to a control.

Figure 5:
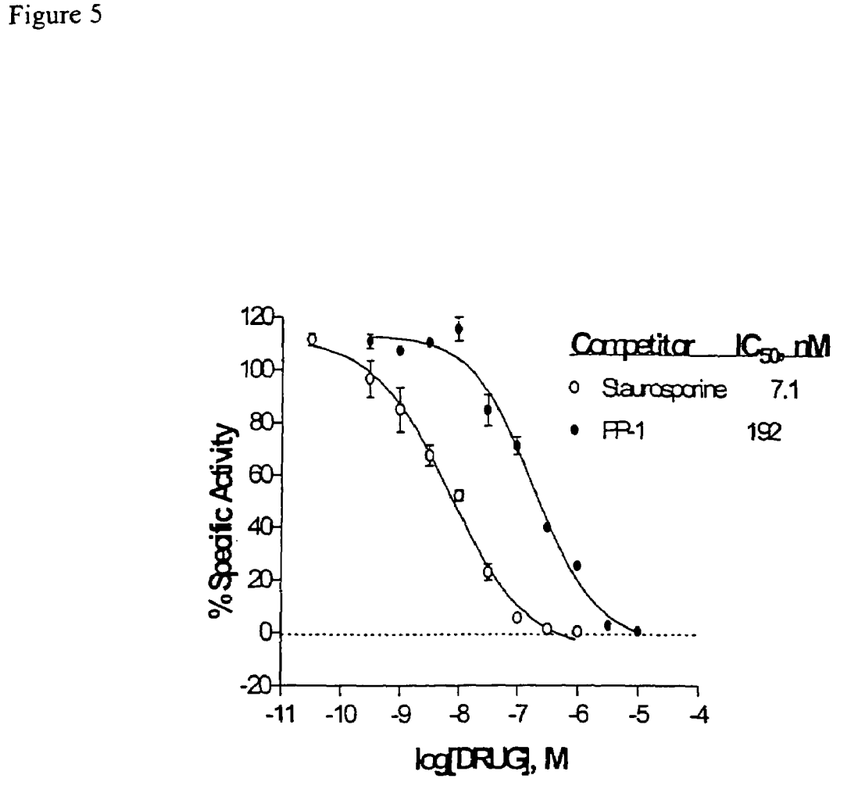
FIG. 5 Comparison of two tyrosine kinase inhibitors, staurosporine and PP-1, on src tyrosine kinase activity measured in a TR-FRET assay using SL-APC/Europium chelate as the FRET pair.

FIG. 5 illustrates the detection of phosphorylated poly-GAT with europium labeled anti-phosphotyrosine IgG (PY20) and SL-APC labeled streptavidin or a commercially available XL-APC labeled streptavidin. Poly-GAT was phosphorylated with a src-tyrosine kinase and then titrated from 0 ng to 12 ng. Positive phosphorylation was measured as a ratio using two wavelengths (620 & 650 nm) as previously described. See, Mathis, *Clin. Chem.*, 41:1391–1397, 1995.

Figure 6:
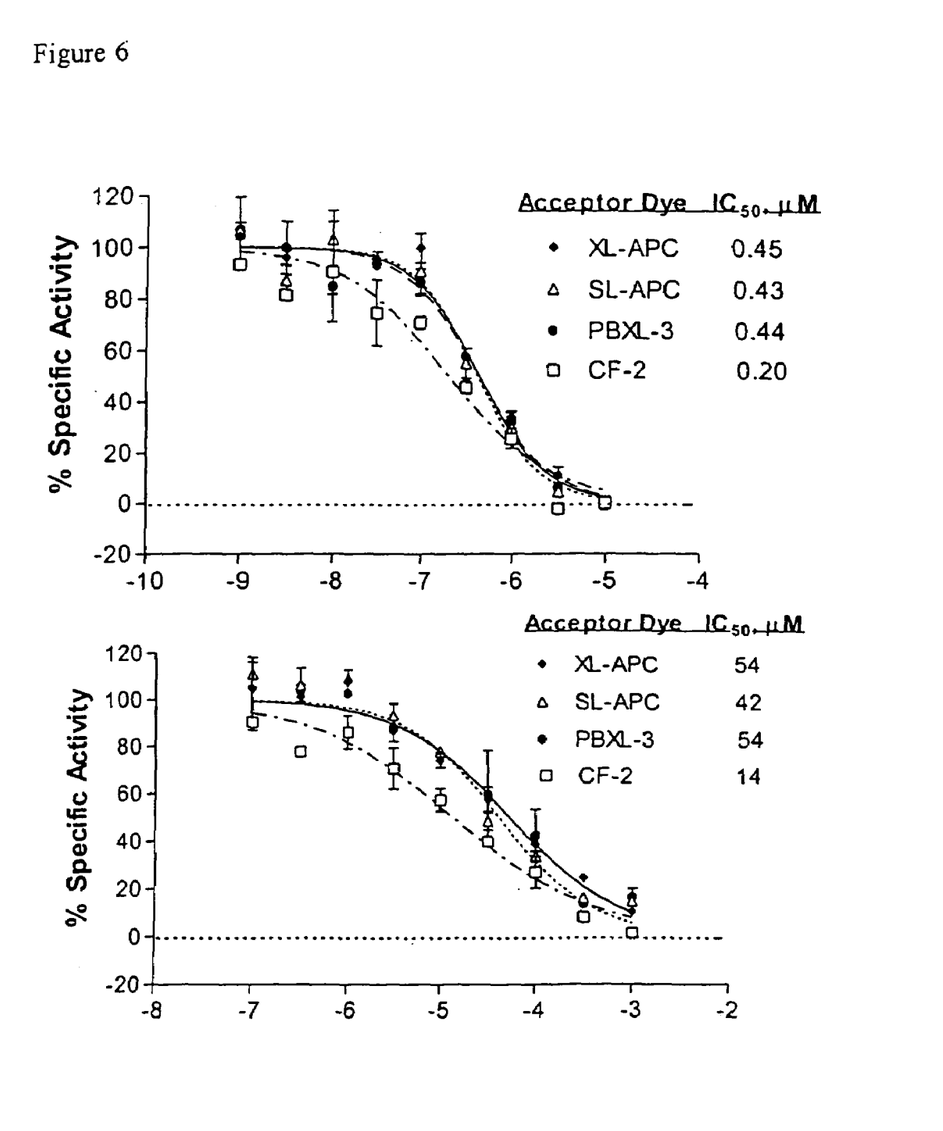
FIG. 6 Comparison of four different Europium acceptor dyes (XL-APC, SL-APC, PBXL-3 and CryptoFluor-2) for Europium chelate emission in a TR-FRET assay titrating the inhibition of β-insulin receptor tyrosine kinase activity with staurosporine (top graph) and 5-iodotubercidin (bottom graph).

FIG. 6 illustrates a comparison of two tyrosine kinase inhibitors, staurosporine, and PP-1, on src tyrosine kinase activity measured in a TR-FET assay using SL-APC/Europium chelate as the FRET pair. FIG. 7 illustrates the comparison of four europium acceptor dyes (XL-APC, SL-APC, PBXL-3, CryptoFlour-2) for europium chelate emission in a TR-FRET assay titrating the inhibition of β-insulin receptor tyrosine kinase activity with staurosporine (top graph) and 5-iodotubercidin (bottom graph). Data obtained with the HTRF assay for tyrosine kinase and with a model system based on the tyrosine kinase assay showed a significant improvement in sensitivity with the cross-linked APC: streptavidin conjugate according to this invention. In addition, the ease of making SL-APC according to this invention over the literature methods are a significant cost advantage to this product.

The sensitivity advantage is important as the industry moves to higher throughput screening formats (e.g., ultra-high throughput screening UHTS) and assay miniaturization. As they move to more tests per plate or to high density arrays, the industry needs better sensitivity to detect the same concentration of analyte. Any improvement in the product sensitivity would be beneficial.

EXAMPLES

In order to facilitate a more complete understanding of the invention, a number of Examples are provided below. However, the scope of the invention is not limited to specific embodiments disclosed in these Examples, which are for purposes of illustration only.

Example 1

Production of High Fluorescent Intensity, Stabilized Allophycocyanin Label

Native allophycocyanin (APC) may be extracted from red or blue-green algae and purified by standard methods. Brejc et al., 1995 *J. Mol. Biol.* 249, 424–440. The purified material is stored as an ammonium sulfate precipitate. Native APC is dialyzed from its ammonium sulfate precipitate form into 50 mM sodium phosphate buffer (pH 7.0) that contains no azide at 4° C. This should be done exhaustively. The dialyzed APC is diluted to 1.5 mg/mL in 50 mM sodium phosphate. EDAC (1-ethyl-3-[3-dimethylaminopropyl]carbodiimide hydrochloride) is added as powder up to 35 mM, and allowed to react for 4 hours at room temperature. The reaction is quenched by mixing with 100 mM glycylglycine until it is dissolved, and the mixture is allowed to react at room temperature or in the cold for at least one hour. This is then qualitatively assayed to determine the degree of cross-linking achieved by diluting the cross-linked APC into 1 M Sodium Perchlorate and 50 mM Tris HCl. The APC absorbance maximum (650 nm peak) should stay greater than the phycocyanin absorbance maximum (620 nm peak) with a A650/620 ratio of no less than 1.2:1. This material is then run on a small polyacrylamide gel to provide roughly 50% of the material in the form of a covalently attached alpha/beta dimeric band with the remaining 50% as separate alpha and beta monomer bands (half the molecular weight).

The resultant material is then precipitated in ammonium sulfate (65% saturation); ammonium sulfate is added at 398 g/L of solution, mixed until dissolved, then stored on ice for at least 2 hours. The amonium sulfate suspension is then centrifuged to collect the precipitate, which is stored as the ammonium sulfate pellet until use at 4° C.

Alternatively, the ammonium sulfate precipitated, cross-linked material may be dialyzed versus 100 mM sodium phosphate (pH 7.2) exhaustively. This is then made to 50 mM sucrose with solid sucrose and aliquotted as desired. The tubes are then flash frozen and freeze dried. The freeze dried powder is then stored until used, preferably at −20° C.

Example 2

Dissociation at Low Pigment Concentration

A major limitation to APC use in specific binding assays is its poor stability under pigment concentrations useful for these binding assays. Native APC broke down when stored at room temperature at a pigment concentration of 500 ng/mL (FIG. 1A). This decay occurred more rapidly than the two hour time point presented (data now shown). APC instability was manifested as a decrease in maximal fluorescence emission intensity and a shift in the fluorescence emission maximum by about 18 nm to the blue.

SL-APC and XL-APC were chemically stabilized to prevent dissociation at the low pigment concentrations normally encountered in a biological assay (Ong & Glazer, 1985). Storage at 500 ng/mL for 2 h at room temperature had little effect on their fluorescence emission spectra in either the absolute peak height or emission maximum (FIGS. 1B and 1C). This increased stability gives the cross-linked APCs the ability to be used in applications for time resolved fluorescence (TRF), flow cytometry and other immunoassay formats.

Figure 2:
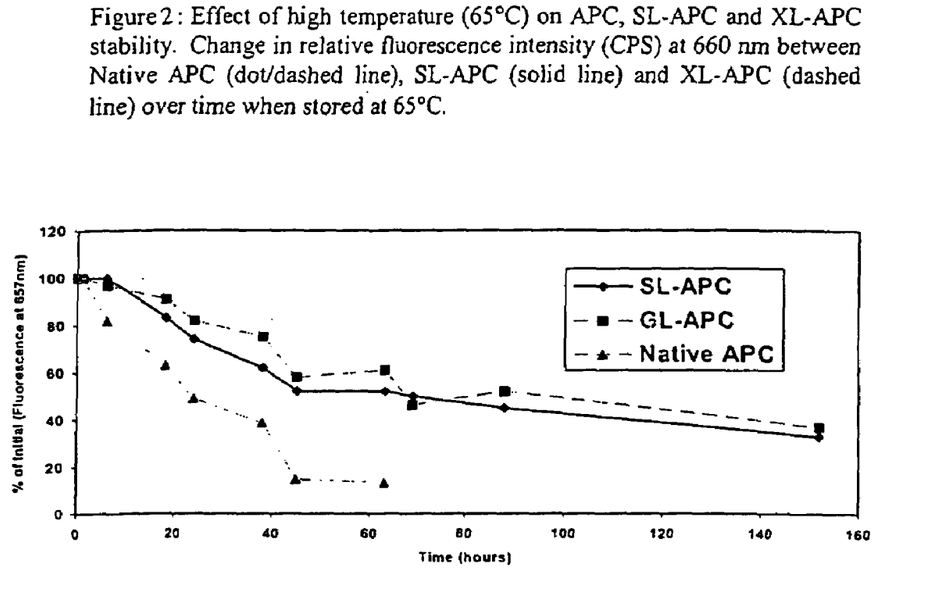
FIG. 2 shows the change in fluorescence intensity over time at high temperature for native APC, SL-APC and XL-APC.

Chemically cross-linked APC, both GL-APC and SL-APC, has increased thermal stability relative to native APC. This allows the use of GL-APC and SL-APC in applications where the temperature needs to be elevated. Stability studies were carried out at 100 μg pigment/mL in phosphate buffered saline (10 mM phosphate (pH 7.0), 150 mM sodium chloride, 0.05% sodium azide) at 65° C. to demonstrate the differences in stability between native APC, SL-APC and GL-APC. SL-APC and GL-APC had comparable temperature stability having little damage for up to 3 days, even retaining 50% of their fluorescent intensity after 60 h incubation at 65° C. (FIG. 2). In contrast, native APC broke down much more rapidly, losing 50% of its fluorescent intensity by 20 h and about 90% after 45 h.

Example 4

Fluorescense Stability in Sodium Perchlorate

One commonly used measure of the stability of cross-linked APC is its response to the application of a chaotrophic salt (Ong & Glazer, 1985; MacColl, et al., 1987 *Phycobiliproteins*, CRC Press, Inc. Boca Raton). Chaotropic salts dissociate native phycobiliproteins into their constituent subunits. Cross-linking of APC provides protection against such chaotrophic salt dissociation. As demonstrated in Table 1, when treated with sodium perchlorate, this chaotrophic salt causes native APC to loose 50% of its fluorescence emission intensity while undergoing about an 18 nm shift to the blue in fluorescence emission (to 642 nm). Both XL-APC and SL-APC maintain their original fluorescence emission maximum while maintaining 92 and 89% of their emission intensity, respectively.

TABLE 1

Effect of chaotropic salt treatment on fluorescence intensity of SL-APC, XL-APC and Native APC at 10 μg/mL. Treated with 1 M Sodium Perchlorate, 50 mM Tris-HCl (pH 7.5). Fluorescence reported as relative fluorescence (cps) at the emission maximum (intact APC emission max at 660 nm; dissociated APC subunit emission max at 642 nm).

| Pigment | Incubation Time (h) | |
|---|---|---|
|  | 0 | 2 |
| SL-APC | $2.70 \times 10^6$ | $2.40 \times 10^6$ |
| XL-APC | $4.37 \times 10^6$ | $4.02 \times 10^6$ |
| Native APC | $3.03 \times 10^6$ | $1.50 \times 10^{6*}$ |

*Reported at the shifted emission max at 642 nm (see FIG. 2A).

Example 5

Stability of SL-APC and XL-APC in 10% DMSO.

In drug screening applications such as time resolved fluorescence, solvents such as DMSO are often employed for sample mobilization. The stability of APC during these screening assays is important for accurate measurement. SL-APC and XL-APC streptavidin conjugates maintain a steady absorbance, providing a constant ability to accept resonance energy transferred from Europium on 10% DMSO treatment. Both dyes maintain their emission maximum at 657 nm. There is an initial decline in fluorescence intensity that quickly stabilizes and then remains relatively constant for several days at this level. FIG. 3 compares the fluorescent stability of GL-APC, a commercial XL-APC and SL-APC over the course of five days. Table 2 compares the change due to 10% DMSO treatment in fluorescence and absorbance over time as a percentage of a control with no DMSO.

TABLE 2

A) GL-APC

| Fluorescence | 657 nm (CPS) | % of Control |
|---|---|---|
| Control | $6.00 \times 10^6$ | 100 |
| Time Zero | $6.00 \times 10^6$ | 99.22 |
| 5 min. | $5.17 \times 10^6$ | 85.47 |
| 90 min. | $5.16 \times 10^6$ | 85.28 |
| 5 day | $4.82 \times 10^6$ | 79.64 |

| Absorbance | ABS 650 nm | % of Control |
|---|---|---|
| Control | 0.98 | 100 |
| 90 min. | 0.98 | 100 |
| 5 day | 0.98 | 100 |

B) XL-APC

| Fluorescence | 657 nm (CPS) | % of Control |
|---|---|---|
| Control | $3.60 \times 10^6$ | 100 |
| Time Zero | $3.55 \times 10^6$ | 99 |
| 5 min | $3.55 \times 10^6$ | 99 |
| 90 min | $3.45 \times 10^6$ | 96 |
| 5 day | $2.70 \times 10^6$ | 75 |

| Absorbance | ABS 650 nm | % of Control |
|---|---|---|
| Control | 0.89 | 100 |
| 90 min. | 0.88 | 99 |
| 5 day | 0.88 | 99 |

C) SL-APC

| Fluorescence | 657 nm (CPS) | % of Control |
|---|---|---|
| Control | $7.75 \times 10^6$ | 100 |
| Time Zero | $6.82 \times 10^6$ | 88 |
| 5 min | $7.02 \times 10^6$ | 91 |
| 90 min | $6.97 \times 10^6$ | 90 |
| 5 day | $6.82 \times 10^6$ | 88 |

| Absorbance | ABS 650 nm | % of Control |
|---|---|---|
| Control | 0.95 | 100 |
| 90 min. | 0.94 | 99 |
| 5 day | 0.95 | 100 |

*APC(C) = competitor's XL-APC

Example 6

Functionality of SL-APC and GL-APC in Homogeneous Time Resolved Fluorescence Tyrosine Kinase Assays Both GL-APC and SL-APC were tested in 96 and 384 well microplates in time resolved fluorescence energy transfer experiments. The detection of a pre-phosphorylated Poly-GAT peptide was used to compare the performance of XL-APC against SL-APC and GL-APC. In this assay, the APC's were used to capture biotinylated Poly-GAT peptide. A src-tyrosine kinase was used to phosphorylate the peptide, which in turn was detected with Europium labeled Anti-Phosphosotyrosine IgG (PY20) (Park, et al, 1999, *Anal. Biochem.* 269: 94–104). Inhibitors, such as staurosporine, can be added to inhibit phosphorylation to generate classical inhibitor response curves. These data show that a titration in 96 well plates of GL-APC, SL-APC and XL-APC generate comparable data when used in the same system to detect the equivalent amount of peptide (FIG. 4; Table 3). Even though this assay (in our hands) has not been optimized to minimize non-specific interactions and maximize signal to noise, SL-APC and GL-APC are very competitive with commercial XL-APC conjugates. Table 3B displays signal to noise data generated from a tyrosine kinase assay in 384 well microplates, which provided comparable results to the 96 well format. Further optimization of this assay should provide better signal to noise ratio (s/n) but the relative performance is expected to remain the same.

TABLE 3

Titration of GL-APC, SL-APC and commercially available XL-APC in a 96 well (top set) and 384 well (bottom set) microplates detecting a fixed amount of phosphorylated peptide (Poly-GAT) as discussed by Park, et al. (1999). Data are reported as a ratio of 650/620 fluorescence emission.

| Conc µg/mL | GL-APC (s/n) | SL-APC (s/n) | XL-APC (s/n) |
|---|---|---|---|
| A) 96 well format | | | |
| 100 | 2.08 | 2.07 | 1.57 |
| 50 | 2.78 | 2.7 | 1.63 |
| 25 | 3.38 | 3.51 | 2.19 |
| 12.5 | 4.03 | 3.89 | 2.5 |
| 6.25 | 4.65 | 3.67 | 2.75 |
| B) 384 well format | | | |
| 100 | 2.53 | 1.81 | 1.33 |
| 50 | 3.02 | 2.43 | 1.84 |
| 25 | 3.86 | 2.74 | 2.32 |
| 12.5 | 4.26 | 3.37 | 2.51 |
| 6.25 | 4.75 | 3.7 | 3.03 |

Example 7

Conjugating Cross-linked SL-APC to Streptavidin

The conjugates are activated with standard crosslinking reagents that are commercially available. SL-APC is activated with a 15 molar excess of sulfo-SMCC and streptavidin (SA) is treated with SATA with a 20 molar excess. SL-APC is offered at a 2.5:1 molar ratio to SA resulting in a conjugate, which is 1 SL-APC to 1 SA. The 1:1 ratio results in a better conjugate for energy transfer experiments (FRET) such as HTRF™ and LANCE™. Conjugates with XL665 (CisBio's XL-APC), are labeled at a 2 SA to 1 APC ratio. Since streptavidin is tetrametric (i.e. being able to bind 4 biotins), the ratios of the conjugate may be commercially important for optimal energy transfer. Resulting data using a tyrosine kinase model show (in detection of a phosphorylated peptide that is biotinylated) a 2 fold improvement in sensitivity, supporting the concept that the conjugate ratio (fluor to protein or F/P ratio) is important. Conjugates according to this invention have four potential biotin binding sites and XL665 has eight. The resulting difference is better energy transfer capability, possibility due to spatial separation (i.e., closer proximity) between Europium and SL-APC due to the conjugation ratio and types of crosslinkers used. This ratio may be contributing to better transfer efficiency as well as the fluorescent intensity differences between SL-APC and XL665.

Example 8

Comparison of SL-APC and XL-APC Streptavidin Conjugates in Two Different Kinase Assays Two alternative cross-linked allophycocyanins (XL-APC and SL-APC) were formatted for tyrosine kinase assays in a time-resolved fluorescence energy transfer (TR-FRET) homogeneous assay format using the VictorII® fluorescent microplate reader (PerkinElmer Life Sciences). The dyes were used in a pair of homogeneous kinase assays in 96-well format using the Victor II reader. An initial comparison of the SL-APC streptavidin conjugate in TR-FRET for the src kinase assay demonstrated an improved sensitivity over a commercially available XL-APC streptavidin conjugate (FIG. 4). Since the encouraging initial experimental results from the kinase experiments indicated that these dyes are highly sensitive and stable, a further exploration of the applicability of SL-APC to several tyrosine kinase assays was completed. The SL-APC dye was formatted into tyrosine kinase assays, and it worked very well and could provide advantages over existing dyes on the market.

SL-APC was evaluated for competitiveness with XL-APC in tyrosine kinase assays under conditions modeled on prior work of Park and colleagues (1999, Anal. Biochem., 269: 94–104). The SL-APC was prepared as described above. Streptavidin conjugates of the alternative dyes were compared in both pp60c-Src tyrosine kinase and β-insulin receptor kinase assays in 96 well plates.

src and β-IRK tyrosine kinase assays. 75 µL of Buffer (50 mM Hepes (pH 7.4), 10 mM $MgCl_2$, 10 µM ATP, 1 mM DTT and 0.1 mM sodium ortho-vanadate (a phosphatase inhibitor) were added to each microwell. For the β-Insulin receptor kinase (IRK) assays, 1 mM $MnCl_2$ addition to the buffer was required. Wells received inhibitor (Staurosporine or PP-1 kinase inhibitors) plus enyzme or just enzyme, then 0.1 to 0.3 µg of substrate were added sequentially. The proper time for polyGAT phosphorylation was determined through an experimental time course experiment (data not shown). Other assay optimization included varying ATP concentration, temperature and enzyme cofactors, such as magnesium and manganese chloride concentrations. Optimal assay conditions were conducted at room temperature for between 90–120 min. The reaction was quenched with 10 mM EDTA. Europium-labeled anti-phosphotyrosine IgG (20 ng/well) and Europium acceptors at 2 µg/well (SL-APC, XL-APC streptavidin conjugates) were then added simultaneously (100 µL) to each well. The components reacted ten minutes and then were read on a Victor II Plate reader using the installed Lance 665 Program.

SL-APC, an alternative acceptor for Europium emission in TR-FRET, was optimized using the Victor II microplate reader in a src kinase assay. SL-APC retains all the characteristics of native APC while obtaining the same stability results as XL-APC in normal assay conditions. This material provides similar performance to XL-APC at a reduced price. SL-APC could provide a low cost alternative to XL-APC in this system if it provided results that did not sacrifice sensitivity.

Optimization of the src kinase assay was done first to determine the proper assay components. The amount of poly-GAT peptide (a polymer of glutamic acid, alanine and tyrosine, which is a substrate for tryosine kinase) was titrated down from 1 µg per well to 0.03 µg/well using either 1 or 2 µg per well of streptavidin:SL-APC conjugate (SA: SL-APC; data not shown). Increasing the amount of SA:SL-APC per test from 1 to 2 µg/well increased the overall signal achieved in each well. This was reflected in an improvement in the signal to noise ratio from 5:1 to 13:1. In these experiments, a SA:SL-APC conjugate with a molar ratio of 1:1 (SA to SL-APC) was utilized along with the Europium chelate linked to anti-phosophotyrosine (pt66) from PerkinElmer. There was little signal intensity difference between 0.03 and 0.1 µg per test in either case. When using the lower SA:SL-APC concentration (1.0 µg/well), a decrease in signal intensity was observed at ≧0.3 µg/well of polyGAT. The 1 µg/well treatment did not provide signal under these detection conditions. For this reason, 2 µg/well of the SA:SL-APC conjugate was utilized for further assay development.

The specific activity of the assay using 0.1 and 0.3 µg of polyGAT peptide in the tyrosine kinase assay was determined in a titration of the inhibitor staurosporine (data not shown). The $IC_{50}$ of staurosprorine determined in the assay was 6.3 and 21.0 nM for the 0.1 and 0.3 µg polyGAT per test, respectively. The $IC_{50}$ at 0.1 µg poly-GAT more nearly matched the literature value of 10–20 nM (Lamers, et al., 1999, *J. Mol. Biol* 285: 712–725). These results indicated that the polyGAT substrate concentration at 0.1 µg/well should be utilized in the src tyrosine kinase assay.

Using the optimized src kinase assay conditions determined above, a comparison of the inhibition of src tyrosine kinase by two different inhibitors, staurosporine and PP-1, was performed using the Europium chelate/SA:SL-APC pair in TR-FRET (FIG. 5). The measured $IC_{50}$ was 7.2 and 192.0 nM for staurosporine and PP-1, respectively. These values matched well with prior experiments as well as with the literature.

Conditions determined for the non-receptor src tyrosine kinase were applied to the insulin receptor tyrosine kinase (β-IRK). SL-APC was compared to the commercial XL-APC conjugates in the TR-FRET assay (FIG. 6). The titration of two inhibitors, staurosporine (Hanke, et al., (1996) "Discovery of a novel, potent and Src-family selective tyrosine kinase inhibitor." *J Biol Chem* 271:695) and 5-iodotubercidin (Massillon, et al., 1994 *Biochem J* 299: 123) versus the fluorescence intensity demonstrated that all of the dyes worked well in the assay and provided very similar curves. The $IC_{50}$ values derived from the curves were very close for XL-APC and SL-APC, for both inhibitors. The signal intensity and the signal to noise ratios (s/n) with these two tyrosine kinase assay systems utilizing different acceptor dyes is summarized in Table 4. The dyes had signal intensity of the same magnitude, with SL-APC edging out SL-APC in signal intensity.

These data illustrate the use of SL-APC as a new acceptor for $Eu^{3+}$ emission used in src and β-insulin receptor tyrosine kinase assays compared to the use of the standard XL-APC as the acceptor dye. SL-APC provided competitive sensitivity to XL-APC without the need for extensive chemical cross-linking and purification.

TABLE 4

Comparison of the maximum signal intensity and the signal to noise ratios (s/n) achieved using streptavidin conjugates of $Eu^{3+}$ acceptor dyes (XL-APC, SL-APC) in time resolved fluorescence energy transfer assays (TR-FRET) formatted for the src and β-insulin receptor tyrosine kinases.

| Dye | Kinase | | | |
| --- | --- | --- | --- | --- |
| | pp60c-src | | βIRK | |
| | Signal | s/n | Signal | s/n |
| XL-APC | 3090 | 8.50 | 947 | 10.4 |
| SL-APC | 6200 | 11.70 | 1343 | 10.9 |

Although the foregoing invention has been described in some detail by way of illustration and example for purposes of clarity of understanding, it will be obvious that certain changes and modifications may be practiced within the scope of the appended claims. Modifications of the above-described modes for carrying out the invention that are obvious to persons of skill in medicine, immunology, fluorescent labeling, protein modification and/or related fields are intended to be within the scope of the following claims.

All publications and patent applications mentioned in this specification are indicative of the level of skill of those skilled in the art to which this invention pertains. All such publications and patent applications are herein incorporated by reference to the same extent as if each individual publication or patent application was specifically and individually indicated to be incorporated by reference.

The invention claimed is:

1. In a method for quantitating an analyte by measuring time resolved transfer of fluorescence energy to or from a label quantitatively associated with the analyte, the improvement wherein the energy transferred from donor compounds having the ability to absorb light energy and then transfer this energy to cross-linked allophycocyanin is measured using time-resolved detection of fluorescence emission, and wherein the cross-linked allophycocyanin has not been exposed to strongly chaotropic agents after cross-linking.

2. The method of claim 1, wherein the donor compounds comprise a metal.

3. The method of claim 2, wherein the metal is a lanthanide series metal.

4. The method of claim 3, wherein the lanthanide metal is selected from the group consisting of europium and ruthenium, which may optionally be chelated or in a cryptate.

5. The method of claim 1, wherein non-cross-linked monomeric subunits have not been removed from the cross-linked allophycocyanin molecule.

6. The method of claim 1, wherein the cross-linked allophycocyanin preparation has at least 20% but less than 50% of all alpha subunits of the allophycocyanin molecules linked to no more than one beta subunit.

7. The method of claim 1, wherein the cross-linked allophycocyanin has an absorbance spectrum characterized by a ratio of areas under the absorbance spectrum between 500–700 nm to the area between 250–300 nm of at least 4.

8. The method of claim 1, wherein said method is performed in homogeneous solution or suspension.

9. The method of claim 1, wherein at least two distinct donor species are present, said distinct donor species having different fluorescence lifetimes.

10. The method of claim 9, wherein said distinct donor species absorb at the same wavelength.

11. The method of claim 1, wherein at least two distinct donor species are present, said distinct donor species having different absorption spectra.

12. The method of claim 1, wherein at least two distinct donor species are present, said distinct donor species forming donor/acceptor pairs having the same lifetime and color but being distinguishable by fluorescent intensity.

* * * * *